US009463273B2

(12) United States Patent
Shelton

(10) Patent No.: US 9,463,273 B2
(45) Date of Patent: *Oct. 11, 2016

(54) DRUG DELIVERY APPARATUS AND METHOD FOR AUTOMATICALLY REDUCING DRUG DOSAGE

(71) Applicant: Medallion Therapeutics, Inc., Valencia, CA (US)

(72) Inventor: Brian Michael Shelton, Pasadena, CA (US)

(73) Assignee: Medallion Therapeutics, Inc., Valencia, CA (US)

( * ) Notice: Subject to any disclaimer, the term of this patent is extended or adjusted under 35 U.S.C. 154(b) by 56 days.

This patent is subject to a terminal disclaimer.

(21) Appl. No.: 14/278,194

(22) Filed: May 15, 2014

(65) Prior Publication Data

US 2014/0364839 A1 Dec. 11, 2014

Related U.S. Application Data

(63) Continuation of application No. 13/281,432, filed on Oct. 26, 2011, now Pat. No. 8,747,390, which is a continuation of application No. 11/182,307, filed on Jul. 14, 2005, now abandoned.

(60) Provisional application No. 60/604,999, filed on Aug. 27, 2004.

(51) Int. Cl.
| | |
|---|---|
| *A61M 5/142* | (2006.01) |
| *A61M 5/172* | (2006.01) |
| *A61K 9/00* | (2006.01) |
| *A61M 5/168* | (2006.01) |

(52) U.S. Cl.
CPC ........ *A61M 5/14276* (2013.01); *A61K 9/0097* (2013.01); *A61M 5/172* (2013.01); *A61K 9/0019* (2013.01); *A61K 9/0024* (2013.01); *A61M 5/16827* (2013.01); *A61M 2005/14208* (2013.01); *A61M 2205/3523* (2013.01); *A61M 2205/3561* (2013.01); *A61M 2205/52* (2013.01)

(58) Field of Classification Search
CPC .......... A61M 5/14276; A61M 5/142; A61M 5/172; A61M 2005/14208; A61M 2205/3523
See application file for complete search history.

(56) References Cited

U.S. PATENT DOCUMENTS

| | | | | |
|---|---|---|---|---|
| 3,923,060 A | * | 12/1975 | Ellinwood, Jr. | ........ A61B 5/021 128/DIG. 1 |
| 4,285,799 A | * | 8/1981 | de Nora | .................... C25C 7/02 204/290.09 |
| 4,373,527 A | * | 2/1983 | Fischell | ............ A61M 5/14276 128/903 |
| 4,443,218 A | * | 4/1984 | DeCant, Jr. | ........ A61M 5/14276 128/DIG. 12 |
| 4,457,751 A | | 7/1984 | Rodler | |
| 4,785,799 A | | 11/1988 | Schoon et al. | |
| 5,084,021 A | | 1/1992 | Baldwin | |
| 5,119,832 A | | 6/1992 | Xavier | |
| 5,178,603 A | | 1/1993 | Prince | |
| 5,219,330 A | * | 6/1993 | Bollish | ................. A61M 5/172 128/DIG. 12 |
| 5,458,631 A | | 10/1995 | Xavier | |

(Continued)

*Primary Examiner* — Andrew Gilbert
(74) *Attorney, Agent, or Firm* — Henricks, Slavin, Holmes LLP

(57) ABSTRACT

A drug delivery device which includes a fluid drug reservoir, a catheter, a controllable fluid transfer device, e.g., a pump mechanism or valve, and a drug delivery control means: The drug delivery control means comprises a controller, e.g., a microprocessor or microcontroller which is operable to automatically reduce the rate of drug delivery over a certain reduction interval (e.g., multiple days) from an initial dosage value to a final dosage value.

15 Claims, 4 Drawing Sheets

(56) References Cited

U.S. PATENT DOCUMENTS

| | | | | |
|---|---|---|---|---|
| 5,468,222 A | * | 11/1995 | Altchuler | A61M 5/14 604/500 |
| 5,609,575 A | | 3/1997 | Larson et al. | |
| 5,681,285 A | * | 10/1997 | Ford | A61M 5/172 604/151 |
| 5,685,844 A | * | 11/1997 | Marttila | A61M 5/172 604/65 |
| 6,010,483 A | * | 1/2000 | Spencer | A61M 5/172 604/151 |
| 6,231,560 B1 | | 5/2001 | Bui et al. | |
| 6,261,267 B1 | | 7/2001 | Chen | |
| 6,562,001 B2 | | 5/2003 | Lebel et al. | |
| 6,579,280 B1 | * | 6/2003 | Kovach | A61M 5/14276 604/891.1 |
| 6,599,281 B1 | | 7/2003 | Struys et al. | |
| 7,031,772 B2 | | 4/2006 | Condie et al. | |
| 8,747,390 B2 | * | 6/2014 | Shelton | A61K 9/0097 604/503 |
| 2003/0036744 A1 | | 2/2003 | Struys et al. | |
| 2003/0050621 A1 | | 3/2003 | Lebel et al. | |
| 2003/0204274 A1 | * | 10/2003 | Ullestad | A61M 5/14276 700/90 |
| 2006/0047270 A1 | | 3/2006 | Shelton | |
| 2008/0172044 A1 | | 7/2008 | Shelton | |

* cited by examiner

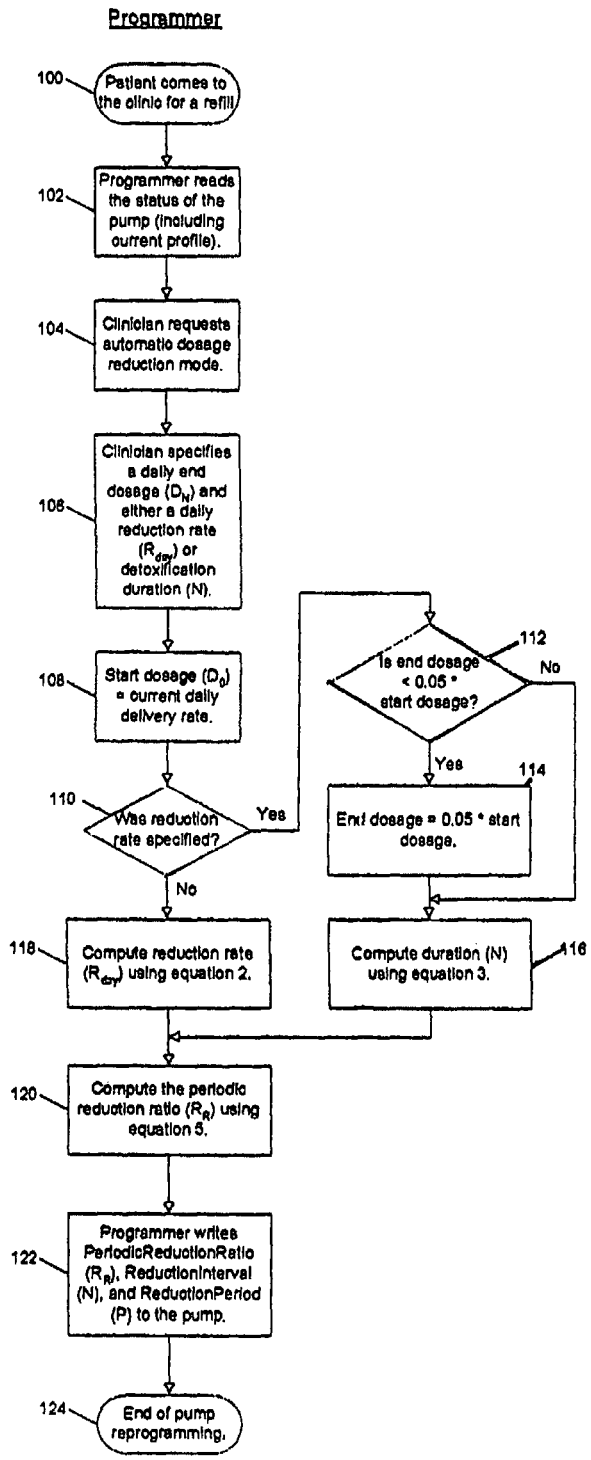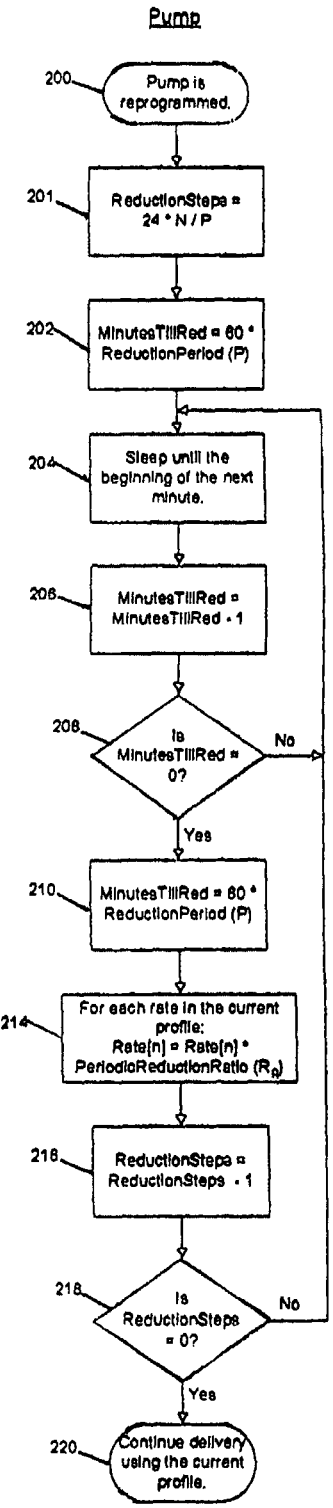
Figure 4
Figure 5

DRUG DELIVERY APPARATUS AND METHOD FOR AUTOMATICALLY REDUCING DRUG DOSAGE

RELATED APPLICATIONS

This application is a continuation of U.S. application Ser. No. 13/281,432, filed Oct. 26, 2011, now U. S. Pat. No. 8,747,390, which is a continuation of U.S. application Ser. No. 11/182,307, filed Jul. 14, 2005, now abandoned, which claims the benefit of U.S. Provisional Application 60/604,999, filed on Aug. 27, 2004, which is incorporated herein by reference.

FIELD OF THE INVENTION

This invention relates generally to medical devices for delivering a medication, or drug, to a body site at flow rates and times specified by a stored drug delivery profile. More particularly, this invention relates to such devices which can operate to automatically gradually modify rates of drug delivery to achieve a desired target dosage.

BACKGROUND OF THE INVENTION

Various implantable drug delivery devices are known in the art which can be programmed to deliver a drug to a body site for infusion at flow rates and times dictated by a stored drug delivery profile. Such delivery devices typically include a refillable reservoir for storing a fluid drug and a controllable fluid transfer device (e.g., a pump or valve) for transferring fluid from the reservoir to a catheter for delivery to the body site. The drug delivery profile comprises a data set specifying a schedule of flow rates for a periodic cycle, or period, of a certain duration. For example, the duration of a period can be twelve hours, twenty four hours, or one week, etc. The particular profile used to control drug delivery is typically specified by the patient's clinician and depends upon several factors including the particular drug formulation being delivered, the patient's condition, the therapy being administered, etc.

The delivery profile is typically stored in the medical device at the time of implanting and can thereafter be modified by a clinician (using an external controller or programmer) when the patient periodically visits for a refill/checkup, e.g., once per month.

In the course of certain drug therapies, it may be desirable to increase or reduce the drug dosage delivered to the patient. For example, in some situations, it may be helpful to reduce or terminate drug administration for a limited period in order to increase the patient's sensitivity to the drug. In still other situations, it may be desirable to terminate delivery of a drug as an initial step in preparation for changing the drug formulation.

For illustrative purposes, in situations where a therapeutic decision has been made to reduce or eliminate delivery of a certain drug, it is generally desirable to reduce the drug dosage gradually. This gradual reduction, which is sometimes referred to as a detoxification procedure, is relatively easy to administer if the patient is available to the clinician on a frequent basis, e.g., daily. However, in the use of implanted drug delivery devices, patients typically visit their clinicians infrequently, e.g., once per month, and it has therefore been inconvenient and impractical to administer a drug modification program. The present invention is directed to an implantable drug delivery apparatus and method of operation which facilitates the automatic gradual modification, e.g., reduction of drug delivery over an extended interval, e.g., many days.

SUMMARY OF THE INVENTION

The present invention relates to a drug delivery device which includes a fluid drug reservoir, a catheter, a controllable fluid transfer device, e.g., a pump or valve mechanism, and a drug delivery controller. The controller, e.g., a microprocessor, is operable in accordance with the invention, to automatically gradually reduce the rate of drug delivery specified by a stored delivery profile from a current dosage value to a targeted final dosage value.

In accordance with a preferred embodiment, dosage reduction is achieved over an interval comprised of multiple periods, where a period may, for example, comprise 4, 12, or 24 hours. An initial delivery profile specifies an initial delivery rate (or rates). Delivery rates for each subsequent period within the reduction interval are determined by applying a calculated reduction rate (typically a percentage) to the delivery profile for the preceding period. In this manner, the initial delivery profile is incrementally reduced in steps to ultimately achieve a delivery profile specifying the desired final dosage value.

For example, in a preferred embodiment, a clinician may specify a final dosage value and the duration of the reduction interval (which can be expressed in number of periods). Based on this information and the initial dosage information contained in the stored initial delivery profile, a system in accordance with the invention operates to calculate a reduction rate which is then used to periodically reduce the delivery rates until the rates appropriate to the final dosage value are reached.

The preferred embodiment also enables the clinician to alternatively specify a periodic (e.g., daily) dosage reduction rate thus enabling the system to then calculate the duration of the reduction interval (e.g., number of days).

Although in many applications, it suffices to calculate and reduce delivery rates on a daily basis, it is recognized that for more rapid dosage reduction, or detoxification, delivery rates can be reduced more frequently by partitioning the 24 hour daily period into subperiods of, for example, 2 hours, 4 hours, or 8 hours.

BRIEF DESCRIPTION OF THE FIGURES

FIG. 4 is a flow chart depicting an algorithm executable by an external programmer for producing data for an implanted drug delivery device to enable the device to gradually reduce the dosage, i.e., rate of drug delivery, to the patient; and FIG. 5 is a flow chart executable by the implanted drug delivery device.

DETAILED DESCRIPTION

Figure 1:
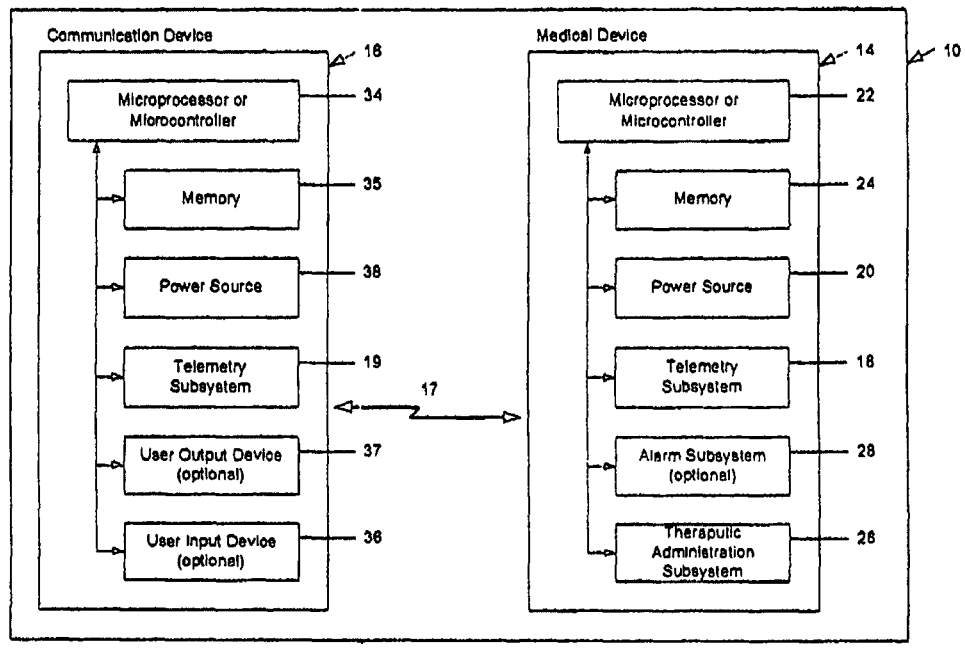
FIG. 1 is a block diagram of an exemplary medical system comprised of an implantable medical device, e.g., a drug delivery device, and an external communication device, or programmer.

Attention is initially directed to FIG. 1 which presents a generalized block diagram of a medical system 10 comprised of at least one medical device 14, e.g., an implantable drug delivery device and an external communication device or programmer 16. The system of FIG. 1 is configured to enable the medical device 14 and the programmer 16 to communicate, e.g., via RF telemetry 17, using telemetry subsystem 18 and telemetry subsystem 19, respectively contained within the devices 14 and 16. The medical device 14 will be assumed herein to comprise a pump implanted in a patient's body for the purpose of delivering a fluid drug to a body site. The programmer 16, on the other hand, is intended to be deployed external to the body and available for use by a physician or clinician or patient to transmit control and/or data signals to the device 14. For example, using the programmer 16, a clinician is able to produce signals which are transmitted via RF link 17 to the medical device 14 to affect its therapeutic performance such as by modifying its drug delivery profile. Systems of the type depicted in FIG. 1, as thus far described are well known. The present invention is directed to a method and apparatus particularly configured to automatically modify a stored delivery profile to reduce the rate of drug delivery to the patient.

As depicted in FIG. 1, a typical medical device 14 in system 10 includes an internal power source 20, e.g., a battery, a controller 22 (sometimes hereinafter referred to as a microprocessor), and a memory 24 associated therewith for storing programs and/or data. The microprocessor 22 operates to execute a stored program to control therapeutic subsystem 26 to controllably deliver a drug to a patient's body site. The device 14 may also include an alarm subsystem 28 controllable by microprocessor 22 to alert the patient or clinician of some monitored event.

Programmer device 16 is shown as including a controller 34 (sometimes hereinafter referred to as a microprocessor which operates in conjunction with memory 35 which stores programs and/or data. The device 16 optionally includes a user input device 36, e.g., a keyboard, and a user output device 37, e.g., a display. The programmer 16 further include aforementioned telemetry subsystem 19 configured to transmit signals to or receive signals from the medical device telemetry subsystem 18. The programmer 16 may further include an internal power source 38 which can comprise a battery or any other suitable conventional power source.

In a typical system 10, the programmer 16 is capable of sending messages to the medical device 14 for use by microprocessor 22 to affect the operation of its therapeutic administration subsystem 26. Additionally, the medical device 14 is typically capable of sending messages to the communication device 16 to report various conditions, e.g., battery status, drug reservoir status, etc. These respective messages sent by the programmer 16 and medical device 14 are handled by the respective telemetry subsystems 19 and 18, each of which is able to transmit and receive RF telemetry signals. Typically, these RF telemetry signals comprise bit streams carried by an RF carrier signal of specified frequency.

Figure 2:
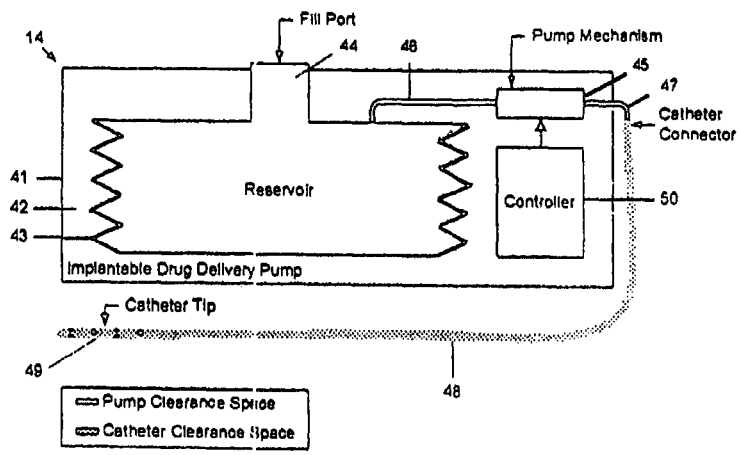
FIG. 2 is a schematic diagram of an exemplary implantable drug delivery device.

FIG. 2 illustrates a typical implantable drug delivery device, or pump, 14 comprising a sealed housing 41 defining an interior volume 42. A reservoir 43 for storing a drug to be delivered is mounted in the housing 41 and has an inlet coupled to a fill port 44. A controllable fluid transfer device 45, e.g., a pump or valve mechanism, couples a reservoir outlet via tube 46 to the proximal end 47 of a catheter 48. The catheter distal end 49 is intended to be implanted proximate to a target site in the patient's body for delivering the drug thereto. FIG. 2 also shows a controller 50 for controlling the fluid transfer device 45. Controller 50 corresponds to controller 22 and associated elements shown in device 14 in FIG. 1.

In typical use, a hypodermic needle (not shown) is used, via fill port 44, to fill the reservoir 43 with a first drug. The fluid transfer device 45 is controlled by controller 50 in accordance with a stored drug delivery profile comprising a set of data which specifies a schedule of drug flow rates over a certain period, e.g., having a duration of twenty four hours.

Figure 3A:
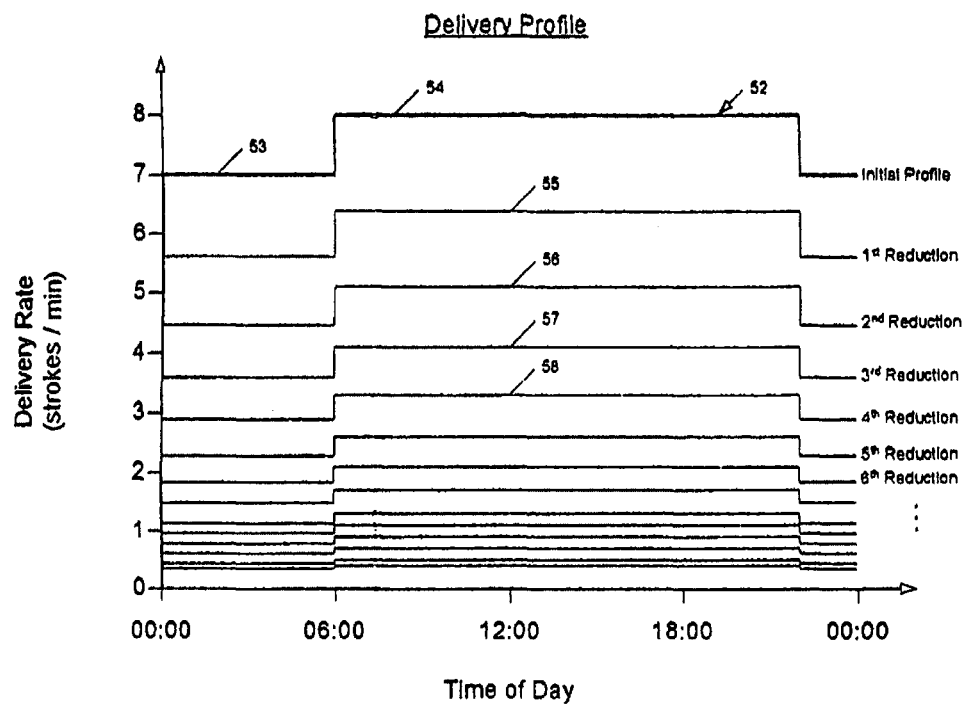
FIG. 3A shows an exemplary initial drug delivery profile for a 24 hour period and successive reductions of said profile in accordance with the invention.

FIG. 3A depicts an exemplary initial daily drug delivery profile 52 defined by data stored in controller 50. Profile 52 specifies a first delivery rate 53 from 00:00 to 06:00 hours and from 22:00 to 00:00 hours and a second delivery rate 54 from 06:00 to 22:00 hours. The exemplary values of the first and second delivery rates are respectively represented in FIG. 3A as 7 and 8 strokes per minute where "strokes per minute" refers to the activity of pump mechanism 45 (FIG. 2). Thus, it can be seen that the profile 52 will cause the pump to produce 11040 strokes/day (i.e., 7 strokes/minute× 60 minutes/hour×8 hours)+(8 strokes/minute×60 minutes/ hour×16 hours). If we assume that pump 40 moves 0.25 microliters of drug per stroke, then the drug dosage, or daily quantity delivered to the patient will equal 2.76 milliliters/ day (i.e., 11040 strokes×0.25 microliters/stroke).

When a dosage reduction operation is initiated in accordance with the present invention, the profile 52 is iteratively processed to successively produce profiles 55, 56, 57, 58, etc. of diminishing amplitude.

Figure 3B:
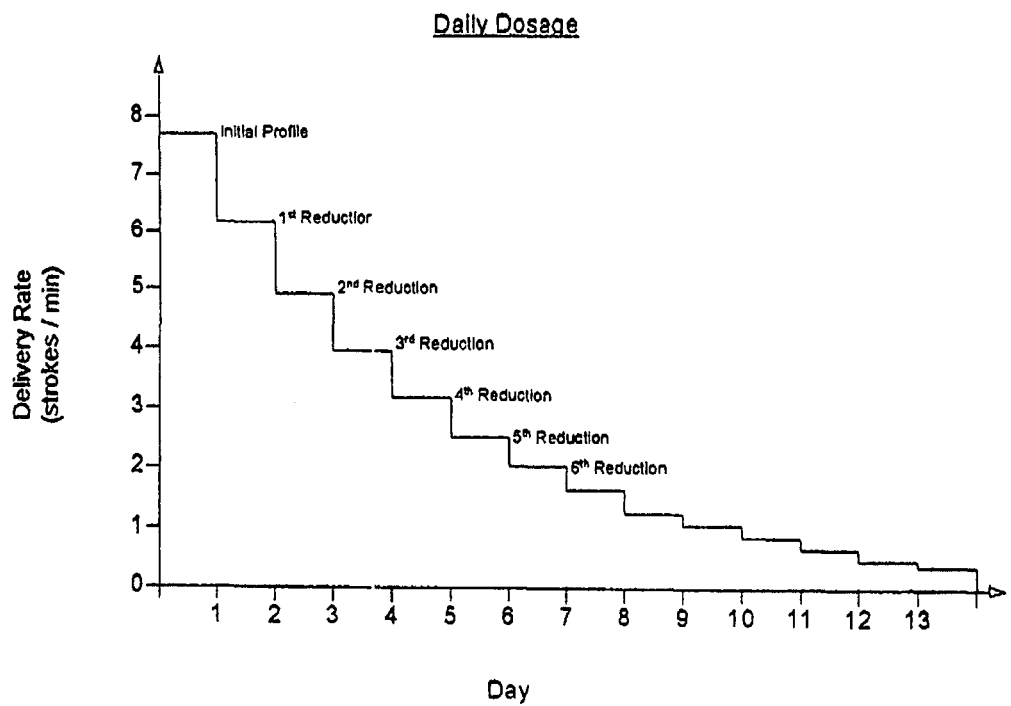
FIG. 3B plots the daily dosage delivered to the patient with respect to FIG. 3A over the full reduction interval showing a reduction of delivery rate occurring once every 24 hours.
Figure 3C:
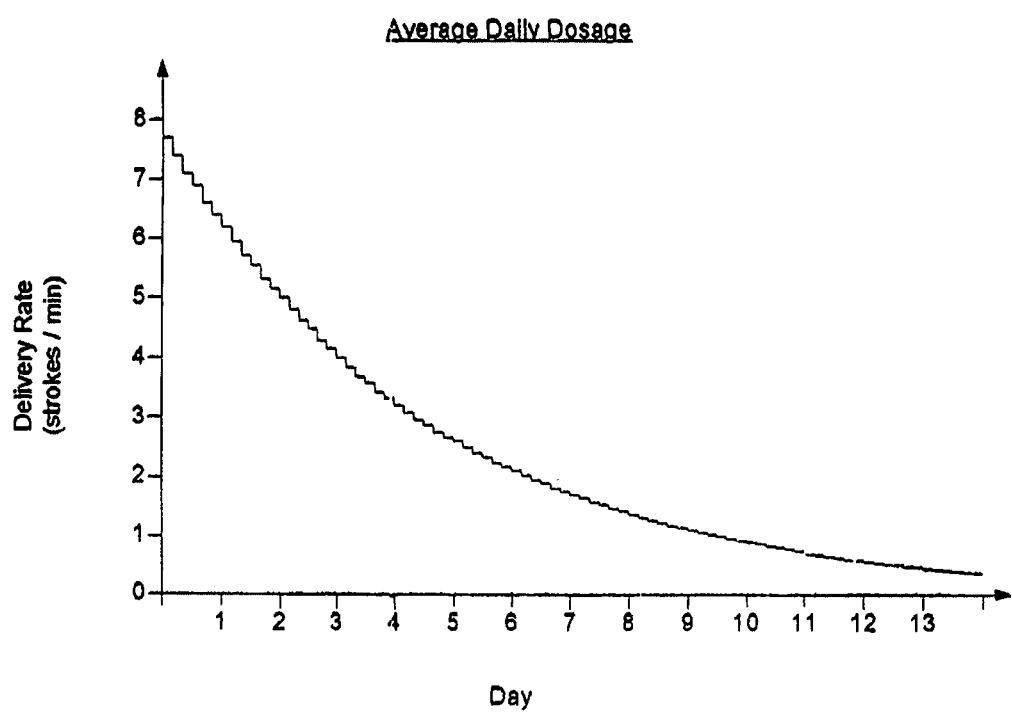
FIG. 3C is similar to FIG. 3B but depicts the full reduction of delivery rate occurring once every four hours rather than once per day.

FIG. 3B depicts the resulting dosage reduction over a multi-day reduction interval. For example, FIG. 3B shows how the daily delivery rate is reduced from an initial value to a final value (shown as zero) over a 14 day interval. Whereas FIG. 3B shows the rate reductions occurring only once per day (i.e., 24 hour period), FIG. 3C demonstrates rate reductions occurring more frequently, e.g., once per 4 hour period.

Attention is now directed to FIG. 4 which comprises a flow chart depicting the functioning of programmer 16 when operated by a clinician to run the automatic drug delivery reduction mode in accordance with the present invention. Block 100 functionally represents the patient's periodic (e.g., monthly) visit to the clinician's office for a checkup and/or drug refill. Block 102 represents the programmer 16 initiating communication with the implanted medical device, or pump, 14 to read status data (including the current drug delivery profile) from the pump's memory 24. Block 104 represents the clinician initiating a dosage reduction, i.e., detoxification operational mode in accordance with the invention.

Before proceeding with the description of the flow chart of FIG. 4, it would be helpful to define certain terms and mathematically develop the task to be accomplished. Let the following parameters by represented by the indicated terms:

$D_0$=Initial daily dosage (ML/day)
$D_N$=Daily dosage on day N (ML/day)
$R_{day}$=Daily reduction rate (%/day)
$R_P$=Periodic reduction rate (%/pd.)
P=Reduction period (hours)
$R_R$=Periodic reduction ratio $(1-R_P)$ (%)
N=Reduction interval (days)

Then $$D_1 = D_0 * (1 - R_{day})$$

$$D_2 = D_0 * (1 - R_{day}) * (1 - R_{day})$$

$$D_N = D_0 * (1 - R_{day})^N \quad (1)$$

If the initial $D_0$ and final $D_N$ daily dosages are known and it is desired that the reduction occur over a fixed reduction interval, equation (1) can be rewritten to find the daily reduction rate.

$$R_{day} = 1 - (D_N/D_0)^{1/N} \quad (2)$$

If the reduction rate Rday, initial dosage $D_0$, and final dosage $D_N$ are known, this equation can be solved for the number of days N.

$$(1 - R_{day}) = (D_N/D_0)^{1/N}$$

$$\text{Log}(1 - R_{day}) = \text{Log}(D_N/D_0)^{1/N}$$

$$N \text{ Log}(1 - R_{day}) = \text{Log}(D_N/D_0)$$

$$N = \text{Log}(D_N/D_0)/\text{Log}(1 - R_{day}) \quad (3)$$

For rapid dosage reduction, it is possible to reduce the dosage several times a day instead of once a day. If this is done, it is still possible to specify the total daily reduction as either a percentage or a ratio. The following equation shows how to convert from a daily reduction ratio to a reduction ratio that is applied every P hours. From equation (1):

$$D_1 = D_0 * (1 - R_{day}) \text{ for a daily reduction}$$

$$D_1 = D_0 * (1 - R_P)^{24/P} \text{ for a reduction every P hours}$$

Therefore:

$$D_0 * (1 - R_{day}) = D_0 * (1 - R_P)^{24/P}$$

$$(1 - R_{day}) = (1 - R_P)^{24/P}$$

$$(1 - R_{day})^{P/24} = (1 - R_P)$$

$$R_P = 1 - (1 - R_{day})^{P/24} \quad (4)$$

The periodic reduction ratio is that fraction by which each delivery rate in the delivery profile is multiplied at the beginning of every reduction interval (P). This is shown in equation (5).

$$R_R = (1 - R_{day})^{P/24} \quad (5)$$

With continuing reference to FIG. 4, block 106 calls for the clinician to enter a final daily dosage value $D_N$ and either a daily reduction rate $R_{day}$ or the reduction interval in days N. Block 108 calls for the programmer microprocessor 34 to read the current dosage value $D_0$ which was retrieved from the pump 14 as part of the current profile in block 104.

Decision block 110 asks if the reduction rate $R_{day}$ was specified. If YES, operation branches to decision block 112 which asks if the final dosage value $D_N$ is less than 0.05 times the initial dosage value $D_0$. If YES, block 114 is executed to adjust the final dosage value $D_N$ to 0.05 times $D_0$. This operation is performed to terminate profile reduction at a value of DN which is clinically insignificant but greater than zero. If profile reduction were allowed to continue until $D_N$ reached zero, the reduction would iterate indefinitely in attempting to asymptotically reach zero. Operation then proceeds to block 116 which computes aforementioned equation (3) to determine the reduction interval N. If decision block 112 yielded a NO, block 114 is skipped.

If decision block 110 yields a NO, operation proceeds to block 118 which computes aforementioned equation (2) to determine the daily reduction rate $R_{day}$.

From either block 116 or 118, operation proceeds to block 120 which computes aforementioned equation (5) to determine the periodic reduction ratio $R_R$. Thereafter (block 122), the programmer 16 transmits various values to reprogram the pump 14 including periodic reduction ratio $R_R$, reduction period P, and the reduction interval N. This action (block 124) completes the activity of the programmer in the execution of the automatic dosage reduction mode in accordance with the invention.

Attention is now directed to FIG. 5 which depicts a flow chart describing the operation of the pump microprocessor 22 in the execution of the automatic dosage reduction mode. The flow chart of FIG. 5 starts with block 200 which represents the pump 14 having been reprogrammed by the operation depicted in FIG. 4. Block 201 calculates the number of reduction steps required. For the sake of clarity in explanation, a typical example will be assumed in which the dosage reduction, or detox, interval will have a duration N of fourteen days and the reduction period P will have a duration of four hours. This assumed example (FIG. 3C) will, of course, require eighty four (i.e., N×24/P) reduction steps to reach the desired final dosage value.

Block 202 sets a timer (MinutesTillRed) to a count value equal to sixty times the reduction period P. The microprocessor 22 can then sleep (block 204) to conserve power until the beginning of the next minute. The MinutesTillRed count is then decremented by one minute (block 206).

Decision block 208 then asks is the MinutesTillRed count equal to zero, or in other words, is it now time to reduce the delivery rate. If NO, operation loops back to block 204. Operation continues to loop through blocks 204, 206, 208 until decision block 208 yields a YES. A YES result from block 208 resets the MinutesTillRed count (block 210) to 6×P.

Block 214 then executes one reduction step by multiplying each rate in the current profile by the periodic reduction ratio $R_{R*}$; i.e., Rate (n)=Rate (n) times $R_R$. Since $R_R$ always has a value less than one, this multiplication will, of course, reduce the value of Rate (n) in the up-dated current profile.

Block 216 then decrements the RedStop count by one. Block 218 then asks if the RedStop count is equal to zero. If NO, operation loops back to block 204. If YES, operation proceeds to block 220 which allows the pump 14 to continue to deliver drug in accordance with the current updated profile.

From the foregoing, it should now be understood that a drug delivery apparatus and method of operation has been disclosed herein for automatically and gradually reducing delivery rates. Although only a single preferred exemplary embodiment has been described, it is intended that the appended claims be interpreted to encompass variations and modifications which will be apparent to those persons skilled in the art.

The invention claimed is:
1. A method delivering drug with a drug delivery device located entirely within a patient, the method comprising the steps of:
  wirelessly receiving delivery data with the drug delivery device located entirely within the patient; and
  without receiving additional delivery data
    (1) supplying drug to the patient for a period of at least 2 hours in accordance with a first stored delivery profile that includes a plurality of delivery times and a plurality of first delivery rates that correspond to the delivery times;

(2) after step (1), supplying drug to the patient for a period of at least 2 hours in accordance with a second stored delivery profile that includes a plurality of delivery times and a plurality of second delivery rates that correspond to the delivery times and are respectively lower than the first delivery rates, and (3) after step (2), supplying drug to the patient for a period of at least 2 hours in accordance with a third stored delivery profile that includes a plurality of delivery times and a plurality of third delivery rates that correspond to the delivery times and are respectively lower than the second delivery rates.

2. A method as claimed in claim 1, wherein wirelessly receiving delivery data comprises wirelessly receiving a periodic reduction ratio with the drug delivery device located entirely within the patient.

3. A method as claimed in claim 1, wherein wirelessly receiving delivery data comprises wirelessly receiving a periodic reduction ratio, a reduction period, and a reduction interval with the drug delivery device located entirely within the patient.

4. A method as claimed in claim 1, wherein wirelessly receiving delivery data comprises wirelessly receiving data based on a current dosage, a final dosage, and a reduction rate with the drug delivery device located entirely within the patient.

5. A method as claimed in claim 1, wherein wirelessly receiving delivery data comprises wirelessly receiving data based on a current dosage value, a final dosage value, and a detoxification duration with the drug delivery device located entirely within the patient.

6. A method as claimed in claim 1, wherein the period during which drug is supplied to the patent in accordance with the first delivery profile is at least about 24 hours.

7. A method as claimed in claim 6, wherein the period during which drug is supplied to the patent in accordance with the second delivery profile is at least about 24 hours.

8. A method as claimed in claim 7, wherein the period during which drug is supplied to the patent in accordance with the third delivery profile is at least about 24 hours.

9. A method as claimed in claim 1, wherein at least two of the first delivery rates are different non-zero delivery rates.

10. A method as claimed in claim 1, wherein supplying drug to the patient comprises supplying drug to the patient with a pump mechanism.

11. A method delivering drug with a drug delivery device located entirely within a patient, the method comprising the steps of:

storing a 24-hour delivery profile that includes one or more delivery rates in the drug delivery device located entirely within the patient;

wirelessly receiving a final daily dosage value with the drug delivery device located entirely within the patient;

wirelessly receiving a reduction rate or a reduction interval with the drug delivery device located entirely within the patient; and without receiving additional delivery profile information with the drug delivery device located entirely within the patient delivering drug to the patient in accordance with the 24-hour delivery profile that include one or more delivery rates, and then delivering drug to the patient in accordance with a reduced 24-hour delivery profile that includes one or more reduced delivery rates that are functions of the one or more delivery rates and either the transmitted final daily dosage value and the transmitted reduction rate or the transmitted final daily dosage value and the transmitted reduction interval, and then delivering drug to the patient in accordance with a further reduced 24-hour delivery profile that includes one or more reduced delivery rates that are functions of the one or more reduced delivery rates and either the transmitted final daily dosage value and the transmitted reduction rate or the transmitted final daily dosage value and the transmitted reduction interval.

12. A method as claimed in claim 11, wherein the 24-hour delivery profile includes at least two non-zero delivery rates that are different than one another.

13. A method as claimed in claim 11, wherein wirelessly receiving a reduction rate or a reduction interval comprises wirelessly receiving a reduction rate with the drug delivery device located entirely within the patient.

14. A method as claimed in claim 11, wherein wirelessly receiving a reduction rate or a reduction interval comprises wirelessly receiving a reduction interval with the drug delivery device located entirely within the patient.

15. A method as claimed in claim 11, wherein delivering drug to the patient comprises delivering drug to the patient with a pump mechanism.

* * * * *